US00PP19301P2

(12) United States Plant Patent
Gutter

(10) Patent No.: US PP19,301 P2
(45) Date of Patent: Oct. 7, 2008

(54) *SAXIFRAGA* PLANT NAMED 'ROCKROSE'

(50) Latin Name: *Saxifraga×arendsii*
Varietal Denomination: Rockrose

(75) Inventor: Martien Everett Gutter, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 4 days.

(21) Appl. No.: 11/800,856

(22) Filed: May 8, 2007

(51) Int. Cl.
*A01H 5/00* (2006.01)

(52) U.S. Cl. ..... Plt./263.1; Plt./226

(58) Field of Classification Search ..... Plt./263.1, Plt./226
See application file for complete search history.

(56) References Cited

PUBLICATIONS

UPOV–Rom GTITM Plant Variety Database, May 2007, GTI Jouve Retrieval Software, citation for 'Rockrose'.*

* cited by examiner

*Primary Examiner*—Annette H Para
*Assistant Examiner*—S. B. McCormick-Ewoldt
(74) *Attorney, Agent, or Firm*—S. Matthew Edwards

(57) ABSTRACT

A new *Saxifraga* plant, particularly distinguished by its rose flower color, early flowering and compact plant habit.

1 Drawing Sheet

Latin name of the genus and species of the plant claimed: *Saxifraga×arendsii.*
Varietal denomination: 'Rockrose'.

BACKGROUND OF THE NEW PLANT

The present invention comprises a new distinct cultivar of *Saxifraga,* botanically known as *Saxifraga×arendsii.*

The new *Saxifraga* is a product of a planned breeding program conducted in Enkhuizen, Netherlands. The new *Saxifraga* cultivar has a compact plant habit, a rose flower color and an early flowering.

The new *Saxifraga* is propagated by cuttings resulting from a single seedling. This seedling originates from a rose flowering selection in *Saxifraga×arendsii* 'Blutenteppich' (not patented), identified as number 'D652.' This selection was made through three cycles of half sib selection. The selection was done in the period April 2001 until March 2003 in Enkhuizen, The Netherlands. The seedling was selected in March 2003 in Enkhuizen.

The present cultivar has been repeatedly asexually reproduced by cuttings in Enkhuizen, Netherlands, since 2003. The distinctive characteristics of this new *Saxifraga* are stable and reproduced true to type in successive generations of asexual reproduction. It takes 23 to 29 weeks to produce a finished plant, depending on the temperature.

The new *Saxifraga* plant is a perennial in all climatic zones in the US.

DESCRIPTION OF THE DRAWING

The new *Saxifraga* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Saxifraga.* The data which defines these characteristics were collected from asexual reproduction carried out in Enkhuizen, Netherlands. The plant history was taken on plants of 30 weeks old. The instant plant was grown in an 11 cm container in a plastic tunnel.

Color references are primarily to the R.H.S. Colour Chart of The Royal Horticultural Society of London.

Plants of the new *Saxifraga* differ primarily from the plants of the originator 'Blutenteppich' in the following characteristics:

Plants of the new variety have uniform rose flowers and a compact growth habit, whereas plants of 'Blutenteppich' have flowers varying in color from light rose to dark red, and a loose growth habit.

TABLE 1

DIFFERENCES BETWEEN THE NEW CULTIVAR 'ROCKROSE' AND A SIMILAR CULTIVAR

| | 'Rockrose' | 'Pixie' (Not patented) |
|---|---|---|
| Length of flower stem | 6-15 cm | 4-10 cm |
| Color of young flower | 63A | 63B |
| Time of flowering | 23-29 weeks after cutting | 26-32 weeks after cutting |

The plant:
*Classification.*—Botanical: *Saxifraga×arendsii.*
Parentage:
*Originator selection.*—'Blutenteppich' (Not patented).
Propagation:
*Type of cutting.*—Terminal cuttings.
*Time to initiate roots.*—12–14 days at 18° C.
*Time to produce a rooted cutting.*—5 weeks.
*Root description.*—Fine, fibrous and white in color.

Plant description:

*General appearance.*—Makes mats of rosettes. Each rosette develops several short branches, and one or more branched flower stems.

*Growth and branching habit.*—Freely branching habit, freely flowering, vigorous.

*Plant height.*—14 cm.

*Plant spread.*—15 cm.

Lateral branches:

*Length.*—3–5 cm.

*Diameter.*—1.2 mm.

*Texture.*—Smooth; pubescent with long hairs: 2–4 mm.

*Internode length.*—2–5 mm.

*Color.*—145C.

The foliage:

*Arrangement.*—Alternate.

*Shape of blade.*—Three-lobed.

*Length, mature leaves.*—0.8–1.1 cm.

*Width, mature leaves.*—0.8–1.0 cm.

*Apex.*—Acute.

*Base.*—Acute.

*Margin.*—Entire.

*Texture.*—Smooth, slightly pubescent.

*Venation pattern.*—Palmate.

*Color of upper surface.*—144A.

*Color of lower surface.*—144B.

*Venation, upper surface.*—145B.

*Venation, lower surface.*—144A.

The petiole:

*Length.*—0.8–1.0 cm.

*Width.*—1.3 mm.

*Color upper surface.*—144C.

*Color lower surface.*—144B.

*Texture.*—Smooth; slightly pubescent.

The flower:

*Inflorescence type.*—Each rosette develops 1–3 branched flower stems.

*Flower type.*—Single, solitary; symmetry: radial symmetric.

*Number of branches per flower stem.*—2–5.

*Number of flowers and flower buds per flower stem.*—2–15.

*Length flower stem.*—6–15 cm.

*Flower position.*—At top of branch.

*Fragrance.*—Absent.

*Flowering season.*—Spring.

*Flower diameter.*—1.5–2.5 cm.

*Lastingness of the bloom.*—40–50 days.

*Lastingness of an individual flower.*—3–6 days.

Flower buds:

*Bud length* (*at stage of showing color*).—3 mm.

*Bud diameter.*—3 mm.

*Bud shape.*—Orbicular.

*Texture.*—Smooth; pubescent.

*Color, just before opening.*—144B, sometimes with 63A on apex.

Petals:

*Quantity.*—5 per flower, imbricate; some flowers develop no or small petals.

*Shape.*—Orbicular.

*Apex.*—Rounded to acuminate.

*Base.*—Shortly attenuate.

*Length.*—8–11 mm.

*Width.*—8–11 mm.

*Margin.*—Entire.

*Texture.*—Smooth.

*Color.*—Upper surface Young flower: 63A. Old flower: 63C.

*Color.*—Lower surface Young flower: 63B. Old flower: 63C.

*Venation pattern.*—Bowed.

*Venation.*—Upper and lower surface Young flower: N66A. Old flower: 63A.

Sepals:

*Quantity.*—5 per flower.

*Shape.*—Ovate.

*Apex.*—Acute.

*Margin.*—Entire.

*Length.*—3–4 mm.

*Width.*—2.5–3.5 mm.

*Color upper surface.*—146B, with some 63A on apex.

*Color lower surface.*—146C.

*Texture upper surface.*—Smooth; slightly pubescent.

*Texture lower surface.*—Smooth, glabrous.

Peduncles:

*Length.*—0.5–2.5 cm.

*Diameter.*—1–1.2 mm.

*Color.*—144A with some anthocyanin 60A.

*Texture.*—Smooth; pubescent.

Reproductive organs:

*Androecium.*—Stamen number: 10, not fused. Filament length: 3–5 mm. Filament shape: Threadlike. Filament color: 154B. Anther shape: Bi-lobed. Anther length: 1.5 mm. Anther color: 149A with anhocyanin 63A. Color of pollen: 2C. Amount of pollen: Normal.

*Gynoecium.*—Pistil number: 2. Pistil length: 5–6 mm. Stigma color: 155A. Style color: 154C. Ovary color: 151B.

Seed development: Seed development has not been observed to date.

Disease/pest resistance: No disease/pest resistance has been observed to date.

What is claimed is:

1. A new and distinct cultivar of *Saxifraga* plant named 'Rockrose,' as substantially illustrated and described herein.

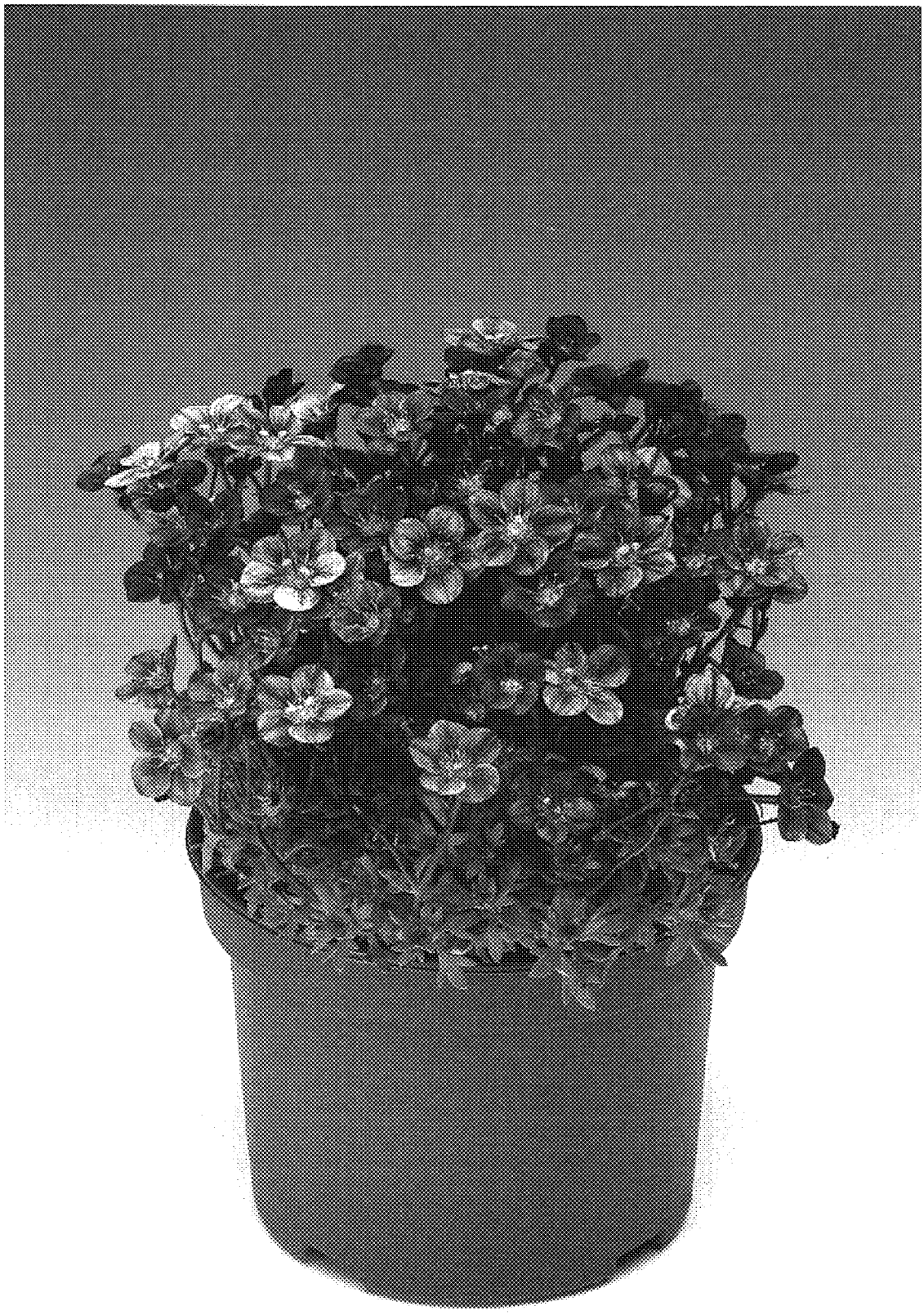

* * * * *